United States Patent
Zhang et al.

(10) Patent No.: US 12,223,650 B2
(45) Date of Patent: Feb. 11, 2025

(54) SYSTEM FOR PREDICTING DISEASE WITH GRAPH CONVOLUTIONAL NEURAL NETWORK BASED ON MULTIMODAL MAGNETIC RESONANCE IMAGING

(71) Applicant: ZHEJIANG LAB, Hangzhou (CN)

(72) Inventors: Yu Zhang, Hangzhou (CN); Chaoliang Sun, Hangzhou (CN); Zhichao Wang, Hangzhou (CN); Huan Zhang, Hangzhou (CN); Haotian Qian, Hangzhou (CN); Tianzi Jiang, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/796,239

(22) Filed: Aug. 6, 2024

(65) Prior Publication Data

US 2024/0394882 A1 Nov. 28, 2024

Related U.S. Application Data

(63) Continuation of application No. PCT/CN2023/124639, filed on Oct. 16, 2023.

(30) Foreign Application Priority Data

Oct. 19, 2022 (CN) .......................... 202211276172.2

(51) Int. Cl.
G06T 7/00 (2017.01)
G16H 30/40 (2018.01)

(52) U.S. Cl.
CPC ........... *G06T 7/0012* (2013.01); *G16H 30/40* (2018.01); *G06T 2207/10088* (2013.01); *G06T 2207/20084* (2013.01); *G06T 2207/30016* (2013.01)

(58) Field of Classification Search
None
See application file for complete search history.

(56) References Cited

U.S. PATENT DOCUMENTS

2022/0122250 A1* 4/2022 Besson ................. G06T 7/0012
2023/0342918 A1* 10/2023 Wang ..................... G16H 30/20

FOREIGN PATENT DOCUMENTS

CN 107658018 A 2/2018
CN 113539435 A 10/2021
(Continued)

OTHER PUBLICATIONS

Goli, Haveesh. "Application of graph convolutional neural networks to Alzheimer's and Parkinson's disease classification." (2021). ( Year: 2021).*

(Continued)

*Primary Examiner* — Samah A Beg
(74) *Attorney, Agent, or Firm* — W&G Law Group

(57) ABSTRACT

A system for predicting disease with graph convolutional neural network based on multimodal magnetic resonance imaging, which extracts the radiomics information of multiple brain regions across modals as the features of nodes from multimodal magnetic resonance data, and extracts the connectomics information between brain regions to form an adjacency matrix. T1-weighted structural images extract cortical information through cortical reconstruction, and resting-state magnetic resonance data are used to calculate amplitude of low frequency fluctuations, regional homogeneity and functional connectivity. Through multimodal data preprocessing, image index extraction and structured data integration, multimodal unstructured magnetic resonance image data are integrated into unified graph-structured data, and the disease is predicted by a graph convolutional neural network method. The system can better integrate the cross-modal physiological indexes of multiple brain regions and (Continued)

the correlation between brain regions and improve prediction ability of the model and generalization ability of the model with different diseases.

8 Claims, 2 Drawing Sheets

(56) References Cited

FOREIGN PATENT DOCUMENTS

| CN | 114334140 A | 4/2022 |
|---|---|---|
| CN | 115116607 A | 9/2022 |
| CN | 115359045 A | 11/2022 |
| EP | 3965117 A1 | 3/2022 |
| WO | 2022147871 A1 | 7/2022 |

OTHER PUBLICATIONS

Subaramya, S., et al. "Graph neural network based Alzheimer's disease classification using structural brain network." 2022 22nd International Conference on Advances in ICT for Emerging Regions (ICTer). IEEE, 2022. (Year: 2022).*

Zheng, Shuai, et al. "Multi-modal graph learning for disease prediction." IEEE Transactions on Medical Imaging 41.9 (2022): 2207-2216. (Year: 2022).*

International Search Report (PCT/CN2023/124639); Date of Mailing: Jan. 22, 2024.

Notice of Allowance(202211276172.2 ); Date of Mailing: Jan. 5, 2023.

Research-on-Brain-Disease-Classification-Method-Based-on-Magnetic-Resonance-Imaging.

Analysis-of-factors-influencing-the-access-to-concomitant-chemo-radiotherapy-in-elderly-patients-with-high-grade-gliomas.

* cited by examiner

SYSTEM FOR PREDICTING DISEASE WITH GRAPH CONVOLUTIONAL NEURAL NETWORK BASED ON MULTIMODAL MAGNETIC RESONANCE IMAGING

CROSS-REFERENCE TO RELATED APPLICATIONS

The present application is a continuation of International Application No. PCT/CN2023/124639, filed on Oct. 16, 2023, which claims priority to Chinese Application No. 202211276172.2, filed on Oct. 19, 2022, the contents of both of which are incorporated herein by reference in their entireties.

TECHNICAL FIELD

The present disclosure relates to the field of neuroimaging data analysis, and in particular, to a system for predicting disease with graph convolutional neural network based on multimodal magnetic resonance imaging.

BACKGROUND

Multimodal magnetic resonance imaging (MRI) has multimodal imaging information, which provides a variety of physiological indicators for studying various diseases. T1-weighted structural images allows segmentation of gray matter and white matter, with cortical reconstruction for extracting cortical information such as cortical volume, thickness, and surface area. Resting-state functional magnetic resonance imaging reflects the neural activity of the brain at rest, and is an important method for studying brain function and brain network connection in recent years. Resting-state magnetic resonance data can be used to calculate Amplitude of low frequency fluctuations (ALFF), Regional homogeneity (ReHo) and Functional connectivity (FC). Among them, ALFF is used to measure the activity of neurons in different brain regions, ReHo describes the synchronization of a certain voxel with its neighboring voxels, and FC can be used to evaluate the functional correlation between brain regions. Diffusion magnetic resonance imaging can detect the microstructure features of white matter and the direction of fiber bundles by measuring the diffusion difference of water molecules. Diffusion magnetic resonance data can be used for diffusion tensor imaging (DTI), and the indexes such as Fractional anisotropy (FA) and Mean diffusivity (MD) can be calculated. It can further be used for neurite orientation dispersion and density imaging (NODDI), and calculating the intra-neurite volume fraction (ICVF) and orientation dispersion index (ODI). Moreover, the fiber connection matrix between brain regions can be obtained through the fiber tracking results at the whole brain level, which can be used to evaluate the structural connectomic between brain regions. Among them, FA reflects the ratio of the anisotropic part of diffusion to the total value of diffusion tensors, MD reflects the range of diffusion movement of water molecules per unit time, ICVF can reflect nerve density, and ODI can quantify the dispersion of neurite orientation.

Graph convolutional neural network (GCN) is a method that can extract features from graph data, thus using these features to classify graph data into nodes and graphs. Through the processing of multimodal magnetic resonance data, the above physiological indexes can be obtained.

At present, the methods of disease prediction based on magnetic resonance data generally only involve single-modal data processing, for example, the method based on Support vector machines, (SVM) automatically classifies schizophrenia patients with the brain surface area and cortical thickness (Yuan X, Yan Z, Zhao Y, et al. Support vector machine-based classification of first episode drug-naïve schizophrenia patients and healthy controls using structural MRI[J]. Schizophrenia Research, 2017, 214), or classifies the patients with gradual freezing disease based on the method of Sparse group lasso (SGL) (Richie-Halford A, Yeatman J D, Simon N, et al. Multidimensional analysis and detection of informative features in human brain white matter[J]. PLoS Computational Biology, 2021, 17(6): e1009136), or classifies patients with post-traumatic stress disorder with ALFF values based on SVM (Yuan M, Qiu C, Meng Y, et al. Pre-treatment Resting-State Functional MR Imaging Predicts the Long-Term Clinical Outcome After Short-Term Paroxtine Treatment in Post-traumatic Stress Disorder[J]. Frontiers in Psychiatry, 2018, 9), and the fusion of multimodal data is still relatively lacking. Multimodal brain imaging indexes have been proved to be closely related to various diseases, including Parkinson's disease (Andica C, Kamagata K, Hatano T, et al. Neurite orientation dispersion and density imaging of the nigrostriatal pathway in Parkinson's disease: Retrograde degeneration observed by tract-profile analysis[J]. Parkinsonism & Related Disorders, 2018:55-60), Alzheimer's disease (Liu X, Guo Z, Ding Y, et al. Abnormal baseline brain activity in Alzheimer's disease patients with depression: a resting-state functional magnetic resonance imaging study[J]. Neuroradiology, 2017, 59(7):709-714), depression (Vythilingam M, Vermetten E, Anderson G M, et al. Hippocampal volume, memory, and cortisol status in major depressive disorder: effects of treatment.[J]. Biological Psychiatry, 2004, 56(2):101-112). Moreover, large-scale brain image data is a kind of unstructured data, making it difficult to conduct automatic and intelligent data mining and analysis. Both medical image data and text data in electronic medical records are common unstructured data in the medical field. Despite the significant advancements of convolutional neural networks in the field of image processing, there are still significant limitations for complex medical images due to the diversity of imaging modals, resolutions and imaging angles. Transforming unstructured image data into structured data through appropriate methods appropriate can facilitate subsequent data mining and analysis

SUMMARY

The object of the present disclosure is to provide a system for predicting disease with graph convolutional neural network based on multimodal magnetic resonance imaging, which can fuse the information of multimodal data and improve the prediction ability of the model and the generalization ability of the model for different diseases.

The present disclosure is realized by the following technical solution: a system for predicting disease with graph convolutional neural network based on multimodal magnetic resonance imaging, which includes the following modules:

A multimodal magnetic resonance data acquisition module configured to extract information in multimodal magnetic resonance data according to the brain atlases. The information includes structural images, resting-state magnetic resonance data and diffusion magnetic resonance data.

A data preprocessing module configured to preprocess the structural images, the resting-state magnetic resonance data and the diffusion magnetic resonance data.

A brain radiomics information extraction module configured to calculate information on volumes, thicknesses and surface areas of a cortex in different brain regions according to the structural images processed by the data preprocessing module; calculate information about amplitude of low frequency fluctuations and regional homogeneity of different brain regions according to the resting-state magnetic resonance data processed by the data preprocessing module; and calculating information about fractional anisotropy, mean diffusivity, intracellular volume fraction and orientation dispersion index of the different brain regions according to the diffusion magnetic resonance data processed by the data preprocessing module.

A brain connectomic information extraction module configured to calculate a functional connection matrix for each subject according to the resting-state magnetic resonance data processed by the data preprocessing module; and calculate a structural connection matrix for each subject according to the diffusion magnetic resonance data processed by the data preprocessing module;

A brain graph structure construction module configured to construct a feature vector for the obtained multimodal information of each brain region by taking each brain region of the brain atlases as a node. The obtained multimodal information includes brain structure indexes of the volumes, the thicknesses and the surface areas of the cortex in the different brain regions extracted from the structural images, brain function indexes of the amplitudes of low frequency fluctuations (ALFF) and regional homogeneity (ReHo) values of the different brain regions calculated from the resting-state magnetic resonance data, and brain diffusion indexes of values of the fractional anisotropy (FA), the mean diffusivity (MD), the intracellular volume fraction (ICVF) and the orientation dispersion index (ODI) of each brain region calculated from the diffusion magnetic resonance data; multiply the normalized functional connection matrix and the normalized structural connection matrix as an adjacency matrix; and construct brain graph structured data G (V, E) based on the adjacency matrix. A node set V is composed of brain regions extracted from the brain atlases, and an edge set E is composed of the adjacency matrices obtained by multiplication.

A graph convolutional neural network model construction module configured to construct a graph convolutional neural network model, train the graph convolutional neural network model by taking the brain graph structured data as a model input and a group label of the subject as a model output, and predict brain diseases by the trained graph convolutional neural network model.

Further, the preprocessing process of the data preprocessing module includes: removing a skull from the structural images to retain only a brain tissue structure; performing head movement correction and time correction on the resting-state magnetic resonance data; and performing denoising, head movement correction and eddy current correction on the diffusion magnetic resonance data.

Further, the brain radiomics information extraction module is further configured to segment gray-white matter on the structural images of the brain tissue structure; perform spatial standardization on the segmented structural images, map the segmented structural images to a unified brain surface template fsaverage, and divide the segmented structural images into the different brain regions according to given brain atlases; and reconstruct, by a freesurfer software, the cortex to obtain the information on the volumes, the thicknesses and the surface areas of the cortex in the different brain regions.

Further, the brain radiomics information extraction module is further configured to perform spatial standardization on the corrected resting-state magnetic resonance data, and linearly register the corrected resting-state magnetic resonance data to the structural image and nonlinearly register the corrected resting-state magnetic resonance data to a unified brain volume template MNI152NLinin2009cAsym; perform denoising, band-pass filtering, regression covariate and spatial smoothing on the registered resting-state magnetic resonance data, and calculate the information of the amplitudes of low frequency fluctuations (ALFF) and the regional homogeneity (ReHo) values in different brain regions are calculated. The amplitudes of low frequency fluctuations (ALFF) have a frequency between 0.01 Hz and 0.1 Hz, and the regional homogeneity (ReHo) values are to be calculated before spatial smoothing.

Further, the brain radiomics information extraction module is further configured to perform inverse spatial standardization on the denoised and corrected diffusion magnetic resonance data, nonlinearly register a standard brain template MNI152NLinin2009cAsym to the structural images of each subject, then linearly register the standard brain template to a diffusion image individual space of each subject, and register the brain atlases to the diffusion image individual space of each subject according to the same mapping; perform a diffusion tensor imaging (DTI) model fitting on the diffusion magnetic resonance data after the inverse spatial standardization, and calculate the fractional anisotropy (FA) and the mean diffusivity (MD) of each brain region; and perform a neurite orientation dispersion and density imaging (NODDI) model fitting on the diffusion magnetic resonance data, and calculate the intracellular volume fraction (ICVF) and the orientation dispersion index (ODI) of each brain region.

Further, the brain connectomic information extraction module is further configured to extract average time series of each brain region based on a standard brain atlas from the preprocessed resting-state magnetic resonance data; calculate a Pearson correlation coefficient of time series between brain regions to obtain a Pearson correlation coefficient matrix between the brain regions; and perform Fisher's Z transformation on the Pearson correlation coefficient matrix to obtain the functional connection matrix of each subject.

Further, the brain connectomic information extraction module is further configured to estimate a response function of the preprocessed diffusion magnetic resonance data, reconstruct a fiber orientation distribution model through constrained spherical deconvolution, and perform whole brain fiber tracking based on the reconstructed fiber orientation distribution model; and screen and normalize a result of fiber tracking based on the brain atlases registered to the diffusion image space to obtain the structural connection matrix of each subject.

Further, the graph convolutional neural network model construction module is further configured to construct the graph convolutional neural network model. The graph convolutional neural network model incudes two graph convolutional neural networks (GCN) layers. A filter uses a Chebyshev convolution kernel of a third order, and a loss function adopts a cross entropy function. The graph convolutional neural network model is trained by using back propagation technology with the multimodal magnetic resonance data of the constructed brain graph structured data as an input and the group label of the subject as an output.

The present disclosure has the beneficial effects that the multimodal physiological indexes of a plurality of brain regions and the correlation between brain regions can be better fused through multimodal data preprocessing, image index extraction and structured data integration, using a deep learning method. Compared with the related art that large-scale brain images are restored and invoked as unstructured data, the brain radiomics information extraction module can integrate the radiomics information in the brain region and construct the graph structure of the brain, so that the multimodal information can be fused, the brain region nodes and brain region connections can be fused, and the prediction ability of the model and the generalization ability of the model for different diseases are improved.

BRIEF DESCRIPTION OF DRAWINGS

In order to more clearly explain the embodiments of the present disclosure or the technical solution in the prior art, the drawings needed in the description of the embodiments or the prior art will be briefly introduced below. Obviously, the drawings in the following description are only some embodiments of the present disclosure, and other drawings can be obtained according to these drawings without creative labor for those skilled in the art.

DESCRIPTION OF EMBODIMENTS

The present disclosure will be further described with reference to the attached drawings. In order to make people in the field better understand the technical solution in this application, the present disclosure will be further explained with the attached drawings. But this is only a part of the embodiment of this application, not the whole embodiment. Based on the specific embodiments described in this application, other embodiments obtained by other people in the field without creative work should fall within the scope of the present disclosure.

Figure 1:
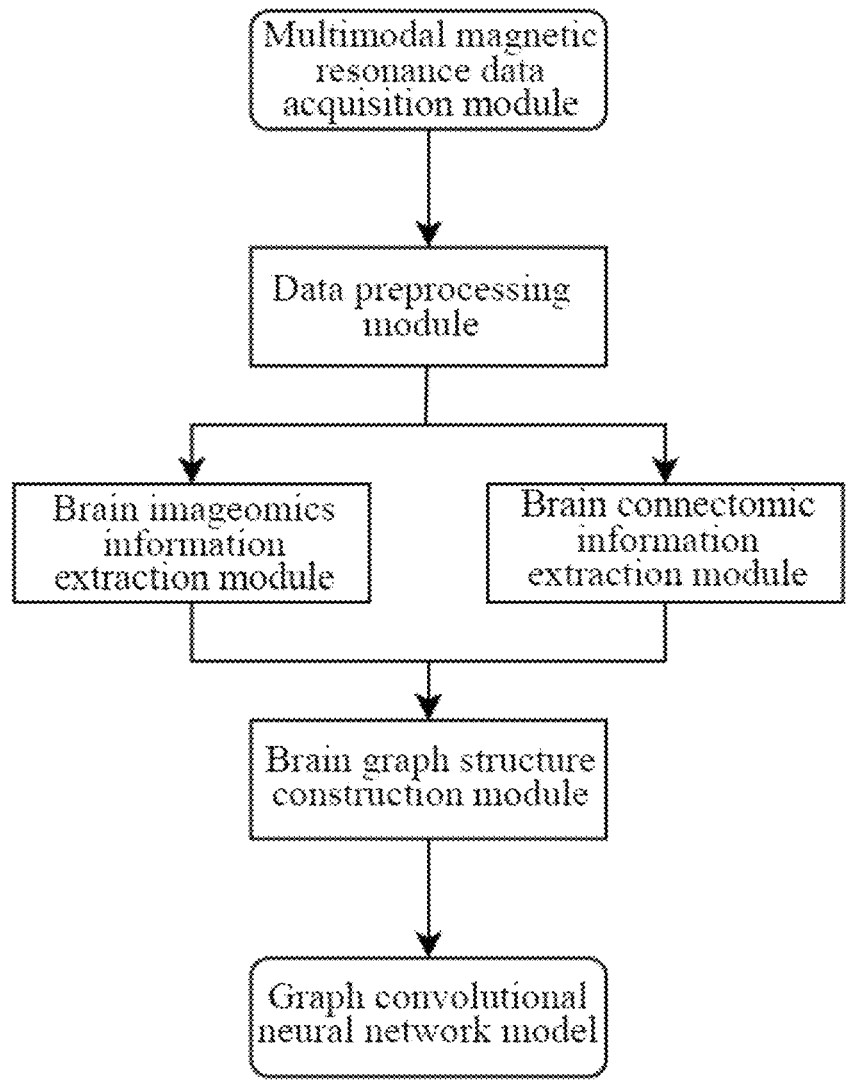
FIG. 1 is a schematic structural diagram of a system for predicting disease with graph convolutional neural network based on multimodal magnetic resonance imaging.

Generally speaking, the present disclosure provides a disease prediction system based on multimodal magnetic resonance imaging, which integrates multimodal magnetic resonance image data into graph-structured data and predicts diseases by using the method of a graph convolutional neural network. Using the multimodal features calculated by the system to predict diseases can fuse the information of multimodal data and improve the prediction ability of the model and the generalization ability of the model under different diseases. The overall system structure is shown in FIG. 1, including a multimodal magnetic resonance data acquisition module, a data preprocessing module, a brain radiomics information extraction module, a brain connectomic information extraction module, a brain graph structure construction module and a graph convolutional neural network model; the multimodal magnetic resonance data acquisition module is used for acquiring brain image data of multimodal magnetic resonance, including structural images, resting-state magnetic resonance data and diffusion magnetic resonance data; the data preprocessing module is used for preprocessing and registering each modal of multimodal brain image data. The data preprocessing of structural image includes removing skull and non-brain tissue, spatial standardization, segmentation of gray matter, white matter and cerebrospinal fluid, cortical reconstruction by FreeSurfer software package, quantification of the function, connectomic and structural attributes of a human brain, three-dimensional reconstruction of structural image, generation of flattened or expanded image, and obtaining anatomical parameters such as cortical thickness, area and gray matter volume. The preprocessing of resting functional magnetic resonance data includes: time layer correction, head movement correction, structural image and functional image alignment, spatial standardization, ICA-AROMA denoising and other steps. After the above steps are completed, the standard spatial resting-state functional magnetic resonance data after ICA-AROMA denoising are used for further regression denoising, including head motion parameters, global signals, white matter signals, cerebrospinal fluid signals and the like. Then, the data is band-pass filtered and spatially smoothed. The preprocessing of diffusion magnetic resonance image data includes: image denoising, distortion correction, signal normalization by extracting b0 image, head movement and eddy current correction. After the above steps are completed, a diffusion model reconstructed for the images based on the data b vector distribution, and the response function and fiber orientation distribution function are calculated to track the fibers of the whole brain. The brain radiomics information extraction module is based on the standard brain atlas, and the data of different modals and different resolutions are registered with the standard brain atlas through the previous preprocessing method, so that the brain imaging information of each modal is calculated in each brain region, including brain structural indexes such as cortical volume, thickness and surface area of different brain regions extracted from the structural image, brain functional indexes such as ALFF and ReHo values of different brain regions calculated in the resting state, and fractional anisotropy (FA), mean diffusivity (MD), intracellular volume fraction (ICVF) and orientation dispersion index (ODI) value and the like of each brain region calculated by diffusion magnetic resonance. The brain connectomic information extraction module is used for calculating connectomics information of each mode between brain regions, including a functional connection matrix calculated by resting-state magnetic resonance data and a structural connection matrix calculated by diffusion magnetic resonance, and multiplying the normalized brain functional connection matrix and the structural connection matrix as an adjacency matrix of a graph model; the brain graph structure construction module is used for taking the radiomics information in the brain region as the node feature and integrating the brain connectomics information as the weight of the edge to construct the data of the graph structure; the graph convolutional neural network model construction module is used for constructing a graph convolutional neural network model and inputting brain graph structured data into the graph convolutional neural network model for disease prediction.

The specific implementation process of the system of the present disclosure is as follows.

The preprocessing process includes: structural image preprocessing, resting-state magnetic resonance data preprocessing and diffusion magnetic resonance data preprocessing. For the structural image preprocessing, the Skull-stripping method of ANTs software is used to remove the skull of the structural image and only retain the brain tissue structure; the resting-state functional magnetic resonance data preprocessing firstly uses the MCFLIRT method of FSL software to correct the resting-state data, and uses the 3dTshift method of AFNI software to correct the time;

secondly, the resting-state data are spatially standardized and registered to the structural image and standard template with ANTs software; then, the resting-state data are denoised by ICA-AROMA, and filtered in a frequency domain of 0.01 Hz-0.1 Hz, and the signals of white matter and cerebrospinal fluid are regressed; finally, a Gaussian kernel a full width at half maximum of 6 mm is used for spatial smoothing. For pre-processing of diffusion magnetic resonance data, firstly, the DWI denoise method of MRtrix3 software is used to denoise diffusion magnetic resonance data; then, the head movement correction method of FSL software is used to correct the head movement; finally, Eddy current correction is carried out by eddy method of FSL.

The process of brain radiomics information extraction includes: structural image node information extraction, resting-state magnetic resonance data node information extraction and diffusion magnetic resonance data node information extraction. For the node information extraction of structural image, the FAST method of FSL software is used to segment the gray-white matter of structural image; secondly, the structural image is spatially standardized by using the non-linear registration method of ANTs software, and mapped to the unified brain volume template MNI152NLin2009cAsym, and divided into different brain regions according to the given brain atlas; then, the cortical information is obtained by the cortical reconstruction method of FreeSurfer software, and the structural image is mapped to the unified brain surface template fsaverage and registered to each brain region; finally, the cortical volumes, thicknesses and surface areas of different brain regions are obtained. For the node information extraction of the resting-state magnetic resonance data, the 3dRSFC and 3dReHo functions of AFNI are used to calculate the ALFF and ReHo values of different brain regions. In particular, the ReHo value should be calculated before spatial smoothing; the node information extraction of diffusion magnetic resonance data includes reverse spatial standardization of diffusion magnetic resonance data, nonlinear registration of the standard brain template MNI152NLinin2009cAsym to the structural image of each subject, linear registration to the diffusion image individual space of each subject, and registration of the brain atlas to each subject's diffusion image individual space according to the same mapping; then, the diffusion magnetic resonance data is subjected to DTI model fitting, and the fractional anisotropy (FA) and the mean diffusivity (MD) of each brain region are calculated; finally, the diffusion magnetic resonance data is subjected to neurite orientation dispersion and density imaging model NODDI fitting by using NODDI Matlab toolbox, and the intracellular volume fraction (ICVF) and orientation dispersion index (ODI) of each brain region are calculated.

The process that the brain connectomic information extraction module is used for extracting connectomic information of resting-state magnetic resonance data specifically includes the following steps: extracting the average time series of each brain region based on a standard brain atlas from the preprocessed resting-state magnetic resonance data; secondly, calculating a Pearson correlation coefficient of the average time series between brain regions, and the obtaining a Pearson correlation coefficient matrix between different brain region; finally, subjecting the Pearson correlation coefficient matrix to Fisher's Z transformation, and the obtaining the functional connection matrix of each subject. The Fisher's Z transformation formula is:

$$f = ar\tan h(r)$$

where r represents the Pearson correlation coefficient of time series, and the range is [−1,1], and f is the result of Fisher's Z transformation.

The process that the brain connectomic information extraction module is used for extracting the connectomic information of diffusion magnetic resonance data specifically includes the following steps: estimating the response function of the preprocessed diffusion magnetic resonance data by using MRtrix3 software and reconstructing a fiber orientation distribution model through constrained spherical deconvolution; secondly, performing whole brain fiber tracking based on the reconstructed model. The number of tracked fibers is 10 million; finally, screening the results of fiber tracking based on a SIFT method, retaining the fiber bundles with physiological significance, normalizing the number of fiber bundle, and counting the number of fiber connections between every two brain regions to obtain the structural connection matrix of each subject.

Figure 2:
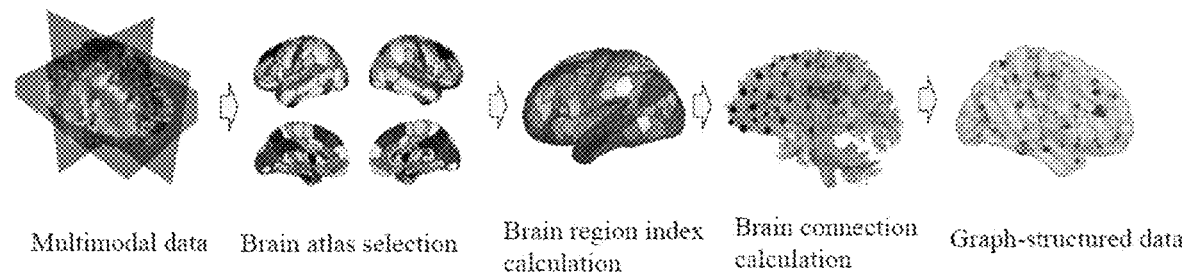
FIG. 2 is a schematic diagram of constructing brain graph structured data proposed by the present disclosure.

The brain graph structure construction module is used to integrate the data of the structured brain image map model. As shown in FIG. 2, each brain region of the selected brain atlases is taken as a node, and the multimodal information of each brain region obtained by the above calculation is used to construct a feature vector, including brain structure indexes such as cortical volumes, thicknesses and surface areas of different brain regions extracted from the structural image, and brain function indexes such as ALFF and ReHo values of different brain regions calculated in the resting state, and brain diffusion indexes of fractional anisotropy (FA), mean diffusivity (MD), intracellular volume fraction (ICVF) and orientation dispersion index (ODI) value of each brain region calculated by diffusion magnetic resonance; secondly, the normalized brain functional connection matrix and structural connection matrix are multiplied as the adjacency matrix of the graph model; thirdly, the graph-structured data G(V, E) is constructed, in which the node set V consists of brain regions extracted from the brain atlas and the edge set E consists of adjacency matrices obtained by multiplication.

Figure 3:
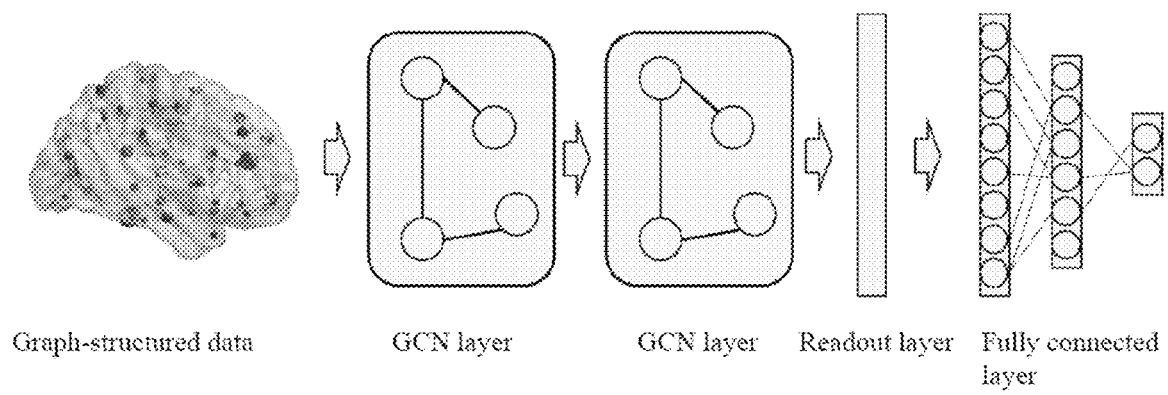
FIG. 3 is a schematic structural diagram of the graph convolutional neural network model proposed by the present disclosure.

The graph convolutional neural network model construction module is used to construct a graph convolutional neural network model, as shown in FIG. 3, which includes two GCN layers, a readout layer and a fully connected layer. The readout layer folds the node representation of each graph into a graph representation, and the fully connected layer is used to make a weighted sum of the previously designed features. A Chebyshev convolution kernel is used for the filter, and the order is 3, where the Chebyshev convolution kernel is:

$$x * g_\theta = \sum_{k=0}^{K} \theta_k T_k(\tilde{L}) x$$

where K represents the order of the Chebyshev convolution kernel, x represents an input features, $g_\theta$ represents a convolution kernel, $\theta_k$ represents the parameter of the filter, $T_k$ represents a Chebyshev polynomial of k order, and $\tilde{L}$ is a regularized Laplacian matrix, which is calculated from the adjacency matrix. The loss function adopts a cross entropy function:

$$\text{Loss} = \sum_{i,k} y_{ik} \log(p_{ik})$$

where $y_{ik}$ represents the $k^{th}$ cognitive function state label corresponding to the $i^{th}$ sample, and $p_{ik}$ is the probability of belonging to the k-th cognitive function state predicted by the graph convolutional neural network model. In the training process, the data sets are randomly divided into a training set, a verification set and a test set according to a ratio of 7:1:2 of the subjects The multimodal magnetic resonance data of the graph structure is used as the input of the graph convolutional neural network model, and the group to which the subject belongs is used as the label as the output of the graph convolutional neural network model. The back propagation technology is used to train the graph convolutional neural network model.

In this application, the term "controller" and/or "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components (e.g., op amp circuit integrator as part of the heat flux data module) that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The above-mentioned embodiments are used to explain, rather than to limit the present disclosure. Any modification and change made to the present disclosure within the scope of protection of the spirit and claims of the present disclosure fall within the scope of protection of the present disclosure.

What is claimed is:

1. A system for predicting disease with graph convolutional neural network based on multimodal magnetic resonance imaging, wherein the system comprises:
    a multimodal magnetic resonance data acquisition module configured to extract information in multimodal magnetic resonance data according to brain atlases, wherein the information comprises structural images, resting-state magnetic resonance data and diffusion magnetic resonance data;
    a data preprocessing module configured to preprocess the structural images, the resting-state magnetic resonance data and the diffusion magnetic resonance data;
    a brain radiomics information extraction module configured to calculate information on volumes, thicknesses and surface areas of a cortex in different brain regions according to the structural images processed by the data preprocessing module; calculate information about amplitude of low frequency fluctuations and regional homogeneity of the different brain regions according to the resting-state magnetic resonance data processed by the data preprocessing module; and calculate information about fractional anisotropy, mean diffusivity, intracellular volume fraction and orientation dispersion index of the different brain regions according to the diffusion magnetic resonance data processed by the data preprocessing module;
    a brain connectomic information extraction module configured to calculate a functional connection matrix for each subject according to the resting-state magnetic resonance data processed by the data preprocessing module; and calculate a structural connection matrix for each subject according to the diffusion magnetic resonance data processed by the data preprocessing module;
    a brain graph structure construction module configured to construct a feature vector for the obtained multimodal information of each brain region by taking each brain region of the brain atlases as a node, wherein the obtained multimodal information comprises brain structure indexes of the volumes, the thicknesses and the surface areas of the cortex in the different brain regions extracted from the structural images, brain function indexes of the amplitudes of low frequency fluctuations (ALFF) and regional homogeneity (ReHo) values of the different brain regions calculated from the resting-state magnetic resonance data, and brain diffusion indexes of values of the fractional anisotropy (FA), the mean diffusivity (MD), the intracellular volume fraction (ICVF) and the orientation dispersion index (ODI) of each brain region calculated from the diffusion magnetic resonance data; multiply the normalized functional connection matrix and the normalized structural connection matrix as an adjacency matrix; and construct brain graph structured data G (V, E) based on the adjacency matrix, wherein a node set V comprises brain regions extracted from the brain atlases, and an edge set E comprises adjacency matrices obtained by multiplication; and
    a graph convolutional neural network model construction module configured to construct a graph convolutional neural network model, train the graph convolutional neural network model by taking the brain graph structured data as a model input and a group label of the subject as a model output, and predict brain diseases by the trained graph convolutional neural network model.

2. The system based on multimodal magnetic resonance imaging according to claim 1, wherein a preprocessing process of the data preprocessing module comprises: removing a skull from the structural images to retain only a brain tissue structure; performing head movement correction and time correction on the resting-state magnetic resonance data; and performing denoising, head movement correction and eddy current correction on the diffusion magnetic resonance data.

3. The system based on multimodal magnetic resonance imaging according to claim 2, wherein the brain radiomics information extraction module is further configured to segment gray-white matter on the structural images of the brain tissue structure; perform spatial standardization on the segmented structural images, map the segmented structural images to a unified brain surface template fsaverage, and divide the segmented structural images into the different brain regions according to given brain atlases; and reconstruct, by a freesurfer software, the cortex to obtain the information on the volumes, the thicknesses and the surface areas of the cortex in the different brain regions.

4. The system based on multimodal magnetic resonance imaging according to claim 2, wherein the brain radiomics information extraction module is further configured to perform spatial standardization on the corrected resting-state magnetic resonance data, and linearly register the corrected resting-state magnetic resonance data to the structural images, and nonlinearly register the corrected resting-state magnetic resonance data to a unified brain volume template MNI152NLinin2009cAsym; perform denoising, band-pass filtering, regression covariate and spatial smoothing on the registered resting-state magnetic resonance data, and calculate the information of the amplitudes of low frequency fluctuations (ALFF) and the regional homogeneity (ReHo) values in the different brain regions, wherein the amplitudes of low frequency fluctuations (ALFF) have a frequency between 0.01 Hz and 0.1 Hz, and the regional homogeneity (ReHo) values are to be calculated before spatial smoothing.

5. The system based on multimodal magnetic resonance imaging according to claim 2, wherein the brain radiomics information extraction module is further configured to perform inverse spatial standardization on the denoised and corrected diffusion magnetic resonance data, nonlinearly register a standard brain template MNI152NLinin2009cAsym to the structural images of each subject, then linearly register the standard brain template to a diffusion image individual space of each subject, and register the brain atlases to the diffusion image individual space of each subject according to the same mapping; perform a diffusion tensor imaging (DTI) model fitting on the diffusion magnetic resonance data after the inverse spatial standardization, and calculate the fractional anisotropy (FA) and the mean diffusivity (MD) of each brain region; and perform a neurite orientation dispersion and density imaging (NODDI) model fitting on the diffusion magnetic resonance data, and calculate the intracellular volume fraction (ICVF) and the orientation dispersion index (ODI) of each brain region.

6. The system based on multimodal magnetic resonance imaging according to claim 5, wherein the brain connectomic information extraction module is further configured to estimate a response function of the preprocessed diffusion magnetic resonance data, reconstruct a fiber orientation distribution model through constrained spherical deconvolution, and perform whole brain fiber tracking based on the reconstructed fiber orientation distribution model; and screen and normalize a result of fiber tracking based on the brain atlases registered to the diffusion image space to obtain the structural connection matrix of each subject.

7. The system based on multimodal magnetic resonance imaging according to claim 1, wherein the brain connectomic information extraction module is further configured to extract average time series of each brain region based on a standard brain atlas from the preprocessed resting-state magnetic resonance data; calculate a Pearson correlation coefficient of time series between brain regions to obtain a Pearson correlation coefficient matrix between the brain regions; and perform Fisher's Z transformation on the Pearson correlation coefficient matrix to obtain the functional connection matrix of each subject.

8. The system based on multimodal magnetic resonance imaging according to claim 1, wherein the graph convolutional neural network model construction module is further configured to construct the graph convolutional neural network model, wherein the graph convolutional neural network model comprises two graph convolutional neural network (GCN) layers, and wherein a filter uses a Chebyshev convolution kernel of a third order, and a loss function adopts a cross entropy function; and train the graph convolutional neural network model by using back propagation technology with the multimodal magnetic resonance data of the constructed brain graph structured data as an input and the group label of the subject as an output.

\* \* \* \* \*